United States Patent [19]

Cairns et al.

[11] 4,260,605
[45] Apr. 7, 1981

[54] NOVEL ALKYLATED PREGNANES, PROCESSES FOR THEIR PREPARATION AND PHARMACEUTICAL COMPOSITIONS CONTAINING SAME

[75] Inventors: James Cairns, Cumbernauld; Robert T. Logan, Lanark; George McGarry, Airdrie; Robert G. Roy, Larkhall; Gilbert F. Woods, Glasgow, all of Scotland

[73] Assignee: Akzo N.V., Arnhem, Netherlands

[21] Appl. No.: 111,941

[22] Filed: Jan. 14, 1980

[30] Foreign Application Priority Data

Jan. 24, 1979 [GB] United Kingdom ............... 02572/79

[51] Int. Cl.³ .......................... A61K 31/56; C07J 5/00
[52] U.S. Cl. ................................ 424/243; 260/397.45; 260/239.55 R; 260/397.4
[58] Field of Search .................. 260/397.45; 424/242, 424/243

[56] References Cited

U.S. PATENT DOCUMENTS 3,045,010  7/1962  Figdor et al. ................... 260/397.47

FOREIGN PATENT DOCUMENTS 941121  11/1963  United Kingdom ............... 260/397.45
1416427  12/1975  United Kingdom ............... 260/397.45
1478968  7/1977  United Kingdom ............... 260/397.45

OTHER PUBLICATIONS

Chemical Abstracts, vol. 66 (1967), Par. 28973(f) relied on. Publication by Ercoli et al.

Primary Examiner—Elbert L. Roberts
Attorney, Agent, or Firm—Haseltine and Lake

[57] ABSTRACT

The present invention relates to novel 21-alkylated steroids of the pregnane series having the formula:

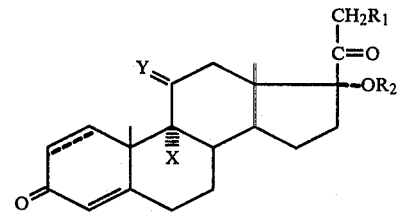

wherein $R_1$ = alkyl (1–4 C); $R_2$ = carboxyacyl (1–18 C); X = H, F or Cl; Y = O, H(OH), H(lower acyloxy), H(F) or H(Cl) with the proviso that Y is not H(F) when X is F; and the dotted line indicates the optional presence of a double bond, to processes for their preparation and to pharmaceutical compositions containing same.

The novel compounds possess strong anti-inflammatory properties, when applied locally and cause little or systemic, thymolytic, adrenolytic and salt-retaining effects.

9 Claims, No Drawings

NOVEL ALKYLATED PREGNANES, PROCESSES FOR THEIR PREPARATION AND PHARMACEUTICAL COMPOSITIONS CONTAINING SAME

The present invention relates to novel 21-alkylated steroids of the pregnane series to processes for their preparation and to pharmaceutical compositions containing same.

More particularly, the invention relates to novel 21-alkylated steroids of the formula:

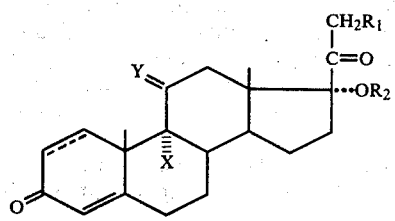

wherein $R_1$=alkyl (1–4 C); $R_2$=carboxyacyl (1–18 C); X=H, F or Cl; Y=O, H(OH), H(lower acyloxy), H(F) or H(Cl) with the proviso that Y is not H(F) when X is F; and the dotted line indicates the optional presence of a double bond. $R_1$ is preferably methyl; $R_2$ is preferably carboxyacyl (1–10 C); X is preferably H and Y is preferably H($\beta$OH).

The novel compounds possess strong anti-inflammatory properties, when applied locally and cause little or no systemic, thymolytic, adrenolytic and salt-retaining effects. Moreover, they have no or low skin-thinning effects, skin-thinning being an undesired side-effect of many known anti-inflammatory steroids. The novel compounds have a very rapid onset of action and are very useful in the treatment of anti-inflammatory conditions especially those associated with the skin and allergic reactions. They can be administered topically in the form of ointments, creams, lotions or sprays or by injection, for instance intra-articularly for the local treatment of inflammation, possibly in combination with other active ingredients. An advantage of the novel compounds in pharmaceutical formulation is that they are better and more soluble in the usual vehicles for topical application, which promotes even distribution on the skin and skin penetration, thus promoting their anti-inflammatory effects.

The compounds within the purview of this invention can be prepared by procedures well known to those skilled in the art.

They may be prepared starting from 20-oxo-17α-oxy steroids of the pregnane series via the Mannich reaction (see e.g. U.S. Pat. Nos. 3,064,017 and 3,069,415) by treating a 20-oxo-17α-hydroxy (or acyloxy) compound of the pregnane series with the salt of an amine, preferably a lower alkyl amine, in the presence of formaldehyde and converting the thus-formed 21-amino-methyl compound into a quaternary ammonium derivative, which is converted into a 21-methylene compound by treatment with a base, and the 21-methylene derivative is either reduced catalytically to the desired 21-methyl compound or converted by 1,4-Grignardation to another 21-alkyl compound. Finally, a present 17α-hydroxy group is acylated according to standard procedures so as to obtain the required 17α-$OR_2$ substituent. A drawback of this procedure is that yields are low.

Another method of introducing a 21-alkyl group into a 20-oxo-17α-oxy steroid of the pregnane series is the method disclosed in U.S. Pat. No. 3,947,478. In this method a 20-oxo-17α-oxy steroid of the pregnane series is alkylated in 21-position by first forming the $\Delta^{20}$-enolate salt with trityl lithium, a lithium dialkylamide, preferably lithium di-isopropylamide, or a Grignard reagent and then reacting the $\Delta^{20}$-enolate salt with an alkyl(1–4 C)halide, preferably an alkyl(1–4 C)iodide, for example methyl iodide. In this procedure the 17α-oxy substituent is preferably not a free hydroxyl group as this may become alkylated during the reaction sequence. Preferably, the 17α-oxy substituent is a 17α-acyloxy group with the formula 17α-$OR_2$, wherein $R_2$ is as defined above.

Starting materials for this alkylation procedure are 20-oxo-17α-oxy pregnanes of the formula:

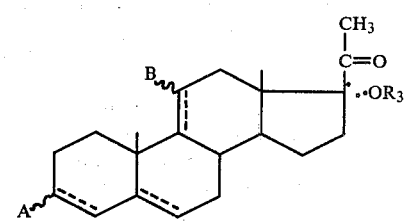

wherein $R_3$=H, alkyl or $R_2$ as defined above, preferably $R_2$; A=a protected hydroxyl group or a protected oxo group; B=H or a protected α- or β-hydroxyl group; and the dotted lines represent the optional presence of one or more double bonds.

During the alkylation procedure, it is preferable to protect an oxygen function at C-3 if one is present by reversible ether formation such as tetrahydropyranyl ether in the case of a 3-hydroxyl group or a $\Delta^{3,5}$-enol ether in the case of a $\Delta^4$-3-oxo grouping, or by acetal formation such as the dimethyl acetal in the case of a 3-oxo group to prevent unwanted alkylation reactions such as O-alkylation which would take place at the same time as 21-alkylation if the starting material contained a free 3-hydroxyl group or 3-acyloxy group or to prevent unwanted C-alkylation reactions from taking place in the α-position to a free 3-oxo group if such were present. It has been found that the 3-O-alkylated products which are formed if a free 3-hydroxyl group or its acyl derivative is present during the alkylation reaction are very difficult to hydrolyse back to the desired 3-hydroxyl group which is a necessary precursor for converting by oxidation to the 3-oxo group in the final products according to the invention.

Similarly, it is necessary to protect an 11-hydroxyl substituent if one is present in the starting material before carrying out the alkylation procedure to prevent the simultaneous formation of an 11-O-alkylated derivative which cannot be readily converted back to the free hydroxyl group. When an 11α-hydroxyl group is present, it is preferable to protect it by reversible ether formation such as the tetrahydropyranyl ether but when an 11β-hydroxyl substituent is present, because of its very sterically hindered position in the steroid molecule it is sufficient to protect it as an ester such as the acetate in which case the acyl group may itself undergo alkylation.

Another method for making the compounds of the present invention is to start from a corresponding 21-hydroxy derivative (see e.g. U.S. Pat. Nos. 3,064,017 and 3,280,159) and eliminating the 21-hydroxy group according to standard procedures well-known to those skilled in the art (see e.g. German Patent Specification No. 1,167,829). The 21-hydroxy group is converted into the 21-sulphonic acid ester group, such as the mesylate, by reaction with an organic sulphonic acid halide such as e.g. methane sulphonic acid chloride, at low temperature (0°–20° C.) in the presence of a base, preferably an organic base such as pyridine, whereafter the 21-sulphonic acid ester group is eliminated by treatment with sodiumiodide in acetic acid anhydride, while heating. A present 17α-hydroxy group is then acylated according to standard procedure so as to obtain the required 17α-OR$_2$ substituent.

A novel and very convenient method for making the compounds of the present invention is to start from a corresponding 17α,21-dihydroxy-20-oxo pregnane compound. The 21-hydroxy group is converted into the 21-sulphonic acid ester group, such as the 21-mesylate, by reaction with the appropriate sulphonic acid halide, such as methane sulphonic acid chloride, whereafter the 21-sulphonate is reacted with a lithium-dialkylcopper compound to give the corresponding 21-alkyl-17α-hydroxy-20-oxo steroid, which is then acylated in 17α-position, for example by treatment with the appropriate acid anhydride in the presence of p-toluene sulphonic acid or 4-dimethylamino pyridine.

This route of making the novel compounds of the present invention from 21-hydroxy pregnanes has the advantage, that it is a short route, that no protecting groups are required for protecting oxo-and/or hydroxy groups in ring A and/or C, including 3-oxo-$\Delta^4$ and 3-oxo-$\Delta^{1,4}$ systems and that the starting materials, such as hydrocortisone, cortisone, prednisolone and prednisone, are readily available.

The conversion of the 21-hydroxy group into the sulphonic acid ester group is carried out as described hereinbefore for the 21-alkyl-21-hydroxy pregnanes. The reaction with lithium-dialkylcopper is carried out in an inert solvent, such as diethyl ether or tetrahydrofuran and preferably dimethylformamide, and at a temperature in the range of between −75° C. and 0° C.

When, after carrying out either of the methods described above, the steroids obtained do not yet have the proper substituents in ring A and/or in 9,11-position as required, these substituents are introduced as yet by methods well-known to persons skilled in the art.

Protecting groups (ether, enol-ether, ester, enol-ester and/or acetal groups) are hydrolysed by methods known in the art.

A 3-hydroxyl group may be oxidised, for example, by Oppenauer oxidation in the case of a $\Delta^5$-steroid to furnish a $\Delta^4$-3-oxo steroid, or with chromic acid in the case of either a 5α- or 5β-3-hydroxy derivative to give the corresponding saturated 3-ketone.

Where a 3-oxo group in the starting material is protected as its acetal derivative, or in the case of a $\Delta^4$-3-ketone, as the enol-ether for the purposes of the alkylation reaction, it is only necessary to hydrolyse it to regenerate the oxo group.

In compounds containing a $\Delta^4$-3-oxo grouping, an additional double bond may be introduced at positions C$_1$-C$_2$ by known chemical means such as by reaction with suitable quinone derivatives or microbiologically with an appropriate microorganism.

A 3-oxo-5α-steroid may be converted to a $\Delta^{1,4}$-3-oxo steroid by means of selenium dioxide or by reaction with a quinone such as dichlorodicyanobenzoquinone or by halogenation at positions 2 and 4 and subsequent dehydrohalogenation by methods known in the art.

A 3-oxo-5β-steroid may be converted into a $\Delta^4$-3-oxo steroid by means of selenium dioxide or by monobromination at position 4 followed by dehydrobromination and the so formed $\Delta^4$-3-ketone may be transformed into the $\Delta^{1,4}$-3-ketone by further reaction with selenium dioxide or dichloro-dicyanobenzoquinone. Alternatively, a 3-oxo-5β-steroid may be converted directly into a $\Delta^{1,4}$-3-ketone by reaction with selenium dioxide or by reaction with a suitable quinone such as dichloro-dicyanobenzoquinone, or by di-halogenation for example di-bromination at positions 2 and 4 and subsequent dehydrohalogenation by methods known in the art.

The microbiological introduction of a double bond at position C$_1$-C$_2$ may be carried out by incubation with a 1,2-dehydrogenating micro-organism, for example *Corynbacterium Simplex, Bacillus sphaericus* or *Bacillus subtilis*.

A $\Delta^{1,4}$-3-oxo steroid can be converted into a $\Delta^4$-3-oxo steroid by $\Delta^1$-hydrogenation e.g. by catalytic hydrogenation in the presence of the homogenous catalyst tris-triphenylphosphine rhodium (I) chloride.

A $\Delta^{9(11)}$-double bond if present may be converted to the 9α-bromo-11β-hydroxy compound or an ester thereof by methods known in the art and then either reduced (debrominated) to the corresponding 9αH-11β-OH compound or transformed under basic conditions into a 9β,11β-epoxide which may be subsequently opened with a halogen acid to give the corresponding 9α-halo-11β-hydroxy derivative.

Introduction of an 11-hydroxyl group may be performed microbiologically, e.g. by incubation with an 11-hydroxylating microorganism such as Curvularia or a Rhizopus.

An 11-hydroxy group may be oxidised to an 11-keto-group, acylated or dehydrated to form a $\Delta^{9(11)}$-double bond.

A $\Delta^{9(11)}$-double bond may be converted to a 9,11-dihalogen derivative such as the dichloride by addition of a halogen such as chlorine.

After elaboration of the $\Delta^{1,4}$-3-oxo group an 11β-acyloxy group, if present, may be hydrolysed to the corresponding 11β-hydroxy derivative under relatively mild conditions with alcoholic alkali and the so formed 11β-hydroxy group may then be oxidised if desired to the corresponding 11-ketone.

A 17α-hydroxy group, if still present, has to be acylated to obtain the compounds of the present invention. A present 11α- or 11β-hydroxyl substituent is temporarily protected by reversible ether formation, such as the tetrahydropyranyl ether or reversible ester formation, such as the acetate, the trifluoracetate or the trichloroethoxyformate, the deprotection being carried out by selective hydrolysis as known in the art, for instance the 11-trifluoracetate can be selectively hydrolysed with sodium formate or potassium carbonate in methanol, particularly in the case of a 3-oxo-$\Delta^{1,4}$-steroid, and the trichloro ethoxyformate with zinc in refluxing methanol. A present 17α-carboxyacyloxy group may be hydrolysed and reacylated, if required. Examples of carboxy-acyloxy groups are those derived from saturated or unsaturated, straight or branched chain, mono-, di- or polybasic, unsubstituted or substituted (for example by hydroxyl, amino or one or more halogen atoms) organic carboxylic acids. Suitable are also carboxy-acyloxy groups derived from cycloaliphatic aromatic, mixed aromatic-aliphatic or heterocyclic carboxylic acids, which can likewise be substituted in the ordinary manner. Specific examples of carboxy-acyloxy groups are acetoxy, propionoxy, caproxy, oenanthoxy, decanoyloxy, decenoyloxy, palmitoxy, trimethylacetoxy, chloroacetoxy, cyclohexylpropionoxy, phenylpropionoxy, phenoxyacetoxy, benzoyloxy. Preferred carboxy-acyloxy groups include acetoxy, propionoxy, butyroxy, isobutyroxy, trimethylacetoxy, valeroyloxy, phenylpropionoxy, cyclohexylacetoxy.

The surprising properties of the novel compounds can be shown in various tests.

HUMAN VASOCONSTRICTION TEST

|  | Compound | | | | |
| --- | --- | --- | --- | --- | --- |
|  | a | b | c | d | e |
| $-\log ED_{50}$ (g/cm$^3$) | 4.0 | 6.0 | 6.8 | 5.5 | 5.7 | a = 11β,17α-dihydroxy-21-methyl-Δ$^4$-pregnene-3,20-dione (known)
b = 11β,17α-dihydroxy-21-methyl-Δ$^4$-pregnene-3,20-dione 17-n-butyrate
c = 11β,17 α-dihydroxy-21-methyl-Δ$^{1,4}$-pregnadiene-3,20-dione 17-propionate
d = 11β,17α-dihydroxy-21-methyl-Δ$^{1,4}$-pregnadiene-3,20-dione 17-pentanoate
e = 11β, 17α-dihydroxy-21-methyl-Δ$^{1,4}$-pregnadiene-3,20-dione 17-pivalate.

The above data indicate the high anti-inflammatory potency of the novel 17-esters in comparison with the corresponding known compound having a free 17α-hydroxy group.

THE RAT SEVEN-DAY INTRACUTANEOUS SKIN THINNING TEST

Male rats strain CFHB, initial body weight 200±3 g, were used in the experiment and divided in seven groups each containing 10 animals, six groups being used for testing the compounds a-f and the seventh group serving as controls.

Each anaesthetised animal in each group received 8 mg of the respective compound injected as 16×0.5 mg suspended in 0.05 ml of suspension fluid into a 4×4 cm area of dorsal shaved skin. The controls received 16×0.05 ml suspension fluid only, injected intravenously.

At autopsy seven days later the spleen, adrenals, thymus and body weight were recorded in addition to the 4×4 cm area of treated skin. Table B summarises the means of the results.

TABLE B

| Cpd. | Final body weight (g) | Treated skin weight (g) | Combined adrenal weight (mg) | Spleen weight (mg) | Thymus weight (mg) |
| --- | --- | --- | --- | --- | --- |
| f | 229 | 1.445 | 21.5 | 445 | 96 |
| g | 227 | 1.410 | 34.7 | 503 | 96 |
| h | 142 | 1.107 | 17.4 | 150 | 65 |
| i | 247 | 1.386 | 37.8 | 647 | 579 |
| b | 249 | 1.660 | 36.3 | 727 | 533 |
| e | 251 | 1.634 | 39.9 | 758 | 557 |
| contr. | 249 | 1.630 | 41.5 | 788 | 612 | f = betamethasone 17-valerate (known)
g = hydrocortisone 17-n-butyrate (known)
h = triamcinolone acetonide (known)
i = 11β,17α-dihydroxy-progesterone 17-n-butyrate (known)
b = 11β,17α-dihydroxy-21-methyl-Δ$^4$-pregnene-3,20-dione butyrate
e = 11β,17α-dihydroxy-21-methyl-Δ$^{1,4}$-pregnadiene-3,20-dione 17-pivalate.

The data indicate that the known compounds have skin thinning effects and that the known compounds f, g and h have systemic effects, whereas the novel compounds are devoid of skin thinning effects and have hardly any systemic effects.

The invention is further illustrated by the following Examples, some of which relate to the preparation of intermediates.

EXAMPLE I (a)

3β,11β,17α-trihydroxy-21-methyl-Δ$^5$-pregnen-20-one

A mixture of 3β,11β,17α-trihydroxy-Δ$^5$-pregnen-20-one (25 g), dimethylamine hydrochloride (20 g), paraformaldehyde (6 g) and 2 N hydrochloric acid (0.6 ml) was refluxed in iso-amyl alcohol (200 ml) for 2¼ hours, then further paraformaldehyde (6 g) was added. After a further hour the solution was cooled, and the crystalline solid which separated was filtered off, washed with ether and dried, to give 3β,11β,17α-trihydroxy-21-dimethylaminomethyl-Δ$^5$-pregnen-20-one hydrochloride (3.0 g).

The filtrate was washed to neutrality with brine, back-extracting the washings with isoamyl alcohol. The organic phase was concentrated to low volume, diluted with ether/methylene chloride and left overnight in the refrigerator. After filtration, the solid was washed with methylene chloride and dried to give a further crop of the amine hydrochloride (0.4 g).

3β,11β,17α-Trihydroxy-21-dimethylaminomethyl-Δ$^5$-pregnen-20-one hydrochloride (3.4 g) was suspended in 1.0 N potassium hydroxide (180 ml) and shaken with ether (360 ml) and methylene chloride (60 ml) for several minutes. The organic layer was then washed neutral with water, dried and evaporated to give the free amine as a crystalline solid. This was dissolved in methylene chloride (36 ml) and ethyl bromide (7.2 ml). The solution was allowed to stand overnight then the quaternary bromide (3.4 g) was filtered off and washed with methylene chloride.

The quaternary bromide salt was dissolved in 25% isopropanol in water (760 ml) and saturated potassium bicarbonate (46 ml) was added. The fine precipitate which formed was extracted into ether (200 ml), and this extract was washed neutral with water, dried and evaporated to give a solid (2.5 g). This was dissolved in isopropanol (128 ml) and hydrogenated over 10% palladium/charcoal (0.3 g) for 30 minutes. The catalyst was removed by filtration and the solution was diluted with water to give a fine solid, which was extracted into methylene chloride (200 ml), dried and evaporated to give a gummy solid (2.4 g). Crystallisation from acetone/hexane gave pure 3β,11β,17α-trihydroxy-21-methyl-Δ$^5$-pregnen-20-one.

(b)

11β,17α-Dihydroxy-21-methyl-Δ$^4$-pregnene-3,20-dione

A solution of 3β,11β,17α-trihydroxy-21-methyl-Δ$^5$-pregnen-20-one (2 g) in dry toluene (20 ml) and cyclohexanone (10 ml) was treated with a solution of aluminium isopropoxide (1 g) in toluene (10 ml). The mixture was heated under reflux for 45 minutes then cooled and treated with a solution of Rochelle salt (4 g) in water (10 ml). The mixture was steam-distilled until the distillate was clear and the product was filtered, dried, and purified on alumina to give 11β,17α-dihydroxy-21-methyl-Δ$^4$-pregnene-3,20-dione (1.5 g).

EXAMPLE II (a)

17α-Hydroxy-21-methyl-Δ$^{9(11)}$-5α-pregnene-3,20-dione-17-acetate

A solution of 17α-hydroxy-Δ$^{9(11)}$-5α-pregnene-3,20-dione 3-dimethylketal 17-acetate (2 g) in sodium-dried tetrahydrofuran (50 ml) was slowly added to a stirred solution of lithium di-isopropylamide (1.5 mole equivalents; prepared from 1.23 ml di-isopropylamine) in tetrahydrofuran (8 ml) under nitrogen at 0° C. The solution was stirred for 30 minutes, allowing it to warm to room temperature, then was again cooled to 0° C., and methyl iodide (10 ml) was added rapidly with vigorous stirring. The cooling bath was again removed and after stirring for 30 minutes the solution was concentrated under vacuum to remove methyl iodide. 80% Acetic acid (25 ml) was added, and the solution was allowed to stand overnight. The product was precipitated as a crystalline solid by the slow addition of water. It was filtered, washed with water and dried to give 1.8 g of 17α-hydroxy-21-methyl-Δ$^{9(11)}$-5α-pregnene-3,20-dione 17-acetate.

(b)

17α-Hydroxy-21-methyl-Δ$^{1,4,9(11)}$-pregnatriene-3,20-dione 17-acetate

17α-Hydroxy-21-methyl-Δ$^{9(11)}$-5α-pregnene-3,20-dione 17-acetate (3.1 g) in toluene (40 ml) was heated under reflux for 18 hours with dichlorodicyanobenzoquinone (4.5 g). The cooled reaction mixture was filtered and the filtrate was washed with water, and potassium carbonate solution, dried over sodium sulphate, and passed through a short column of alumina. The eluate and washings were evaporated to dryness and the residue was dissolved in ethanol (20 ml) containing 10% acetic acid. This solution was refluxed for two hours with Girard's Reagent P (0.6 g), then poured into dilute sodium hydroxide solution, and extracted into methylene chloride. Usual work-up of the extract and crystallisation of the residue from acetone/ether gave 17α-hydroxy-21-methyl-Δ$^{1,4,9(11)}$-pregnatriene-3,20-dione-17-acetate, which was hydrolysed with potassium carbonate in refluxing methanol to give the free 17α-OH compound (1.2 g).

(c)

9β,11β-Epoxy-17α-hydroxy-21-methyl-Δ$^{1,4}$-pregnadiene-3,20-dione

A solution of 17α-hydroxy-21-methyl-Δ$^{1,4,9(11)}$-pregnatriene-3,20-dione (1 g) in dimethylformamide (12 ml) containing perchloric acid (0.2 ml) was stirred at room temperature for two hours with N-bromosuccinimide (0.8 g) in the absence of light. Excess reagent was destroyed with sodium bisulphite solution, and the reaction mixture was poured into water. The product was filtered and dried to give 9α-bromo-11β,17α-dihydroxy-21-methyl-Δ$^{1,4}$-pregnadiene-3,20-dione 11-formate (1.3 g).

The bromo-formate (1.3 g) was suspended in methanol (15 ml) and stirred under nitrogen with a solution of sodium methoxide in methanol (3 ml; 1.1 N) for half an hour. The solution was neutralised with acetic acid and diluted with water. The gummy product was extracted into ether, washed neutral, dried and purified on a short column of alumina, and finally crystallised from ether to give 9β,11β-epoxy-17α-hydroxy-21-methyl-Δ$^{1,4}$-pregnadiene-3,20-dione (0.7 g).

(d)

9α-Fluoro-11β,17α-dihydroxy-21-methyl-Δ$^{1,4}$-pregnadiene-3,20-dione

Gaseous hydrogen fluoride was passed into a mixture of ethanol-free dry chloroform (1 ml) and tetrahydrofuran (2.5 ml) at −40° C. until 1.5 g had been absorbed. 9β,11β-Epoxy-17α-hydroxy-21-methyl-Δ$^{1,4}$-pregnadiene-3,20-dione (0.6 g) in dry chloroform (3 ml) at −40° C. was added to the solution of hydrogen fluoride in chloroform/tetrahydrofuran at −40° C. and washed in with more chloroform (3.5 ml).

The reaction mixture was left in an ice-bath for four hours, and then poured carefully into ice-water containing potassium carbonate (10 g). The solvent was evaporated and the resulting solid was filtered, washed and dried. The crude product was purified on a silica column and crystallised from acetone/ether to give 9α-fluoro-11β,17α-dihydroxy-21-methyl-Δ$^{1,4}$-pregnadiene-3,20-dione (330 mg).

EXAMPLE III (a)

3β,17α-Dihydroxy-21-methyl-Δ$^{9(11)}$-5α-pregnen-20-one 17-acetate

A solution of trityl lithium in dry tetrahydrofuran was added to a stirred solution of 3β,17α-dihydroxy-Δ$^{9(11)}$-5α-pregnen-20-one 3-tetrahydropyranyl ether 17-acetate (3 g) in dry tetrahydrofuran (55 ml) under nitrogen at 0° C. until a slight excess was present. Dry methyl iodide (11 ml) was then added rapidly with vigorous stirring and after 30 minutes the solution was evaporated to dryness under vacuum. The residue was hydrolysed in 80% acetic acid (25 ml) for 30 minutes on a steam-bath, cooled, and the product precipitated with water and isolated via ether/methylene chloride. The washed and dried extract was evaporated and the crude product was purified on a silica column and crystallised from acetone/hexane to give 3β,17α-dihydroxy-21-methyl-Δ$^{9(11)}$-5α-pregnen-20-one 17-acetate (1.5 g).

(b)

17α-Hydroxy-21-methyl-Δ$^{9(11)}$-5α-pregnene-3,20-dione 17-acetate

A solution of 3β,17α-dihydroxy-21-methyl-Δ$^{9(11)}$-5α-pregnen-20-one 17-acetate (1.3 g) in acetone (12.5 ml) was treated with 8 N chromic acid solution (1.8 ml) over ten minutes with external cooling. Excess reagent was destroyed with isopropanol, water was added and the mixture was filtered, washed and dried to give 17α-hydroxy-21-methyl-Δ$^{9(11)}$-5α-pregnene-3,20-dione 17-acetate (1.2 g).

(c)

17α-Hydroxy-21-methyl-Δ$^{1,4,9(11)}$-pregnatriene-3,20-dione 17-acetate

The procedure of Example II(b), when carried out on the product of Example III(b), gave 17α-hydroxy-21-methyl-Δ$^{1,4,9(11)}$-pregnatriene-3,20-dione 17-acetate.

(d)

11β,17α-Dihydroxy-21-methyl-Δ$^{1,4}$-pregnadiene-3,20-dione

A solution of 17α-hydroxy-21-methyl-Δ$^{1,4,9(11)}$-pregnatriene-3,20-dione 17-acetate (2.5 g) in tetrahydrofuran (50 ml) containing perchloric acid was stirred for 1 hour at room temperature with N-bromosuccinimide (1.32 g). Excess reagent was destroyed with sodium bisulphite solution and the reaction mixture poured into water. The product was filtered and dried to give 9α-bromo-11β,17α-dihydroxy-21-methyl-$\Delta^{1,4}$-pregnadiene-3,20-dione 17-acetate (3.15 g).

The bromohydrin (3.15 g) in dimethyl sulphoxide (80 ml) was added to a stirred solution of n-butanethiol (4.7 ml) and chromous acetate (9.5 g) in dimethyl sulphoxide (42 ml) under oxygen-free nitrogen, left overnight at room temperature and then poured into sodium chloride solution. The product was filtered, dried, and recrystallised from methylene chloride/methanol to give 11β,17α-dihydroxy-21-methyl-$\Delta^{1,4}$-pregnadiene-3,20-dione 17-acetate.

EXAMPLE IV (a)

3β,11β,17α-Trihydroxy-21-methyl-5α-pregnan-20-one 3,17-diacetate

A solution of 3β,11β,17α-trihydroxy-5α-pregnan-20-one 3-tetrahydropyranyl ether 11,17-diacetate (2 g) in dry tetrahydrofuran (20 ml) was added to a stirred solution of lithium di-isopropylamide (1.1 mole equivalents) in tetrahydrofuran (20 ml) under nitrogen at −25° C. After 30 minutes, the solution was allowed to warm to −5° C., methyl iodide (10 ml) was added and the reaction mixture allowed to warm to room temperature, after which it was evaporated to dryness under reduced pressure. The residue was dissolved in 80% acetic acid and allowed to stand overnight. Addition of water gave a crystalline solid which was filtered, washed with water, dried and crystallised to give 3β,11β,17α-trihydroxy-21-methyl-5α-pregnan-20-one 11,17-diacetate.

(b)

11β,17α-Dihydroxy-21-methyl-5α-pregnane-3,20-dione 11,17-diacetate

The procedure of Example III(b), when carried out on 3β,11β,17α-trihydroxy-21-methyl-5α-pregnan-20-one 11,17-diacetate gave 11β,17α-dihydroxy-21-methyl-5α-pregnane-3,20-dione 11,17-diacetate.

(c)

11β,17α-Dihydroxy-21-methyl-$\Delta^{1,4}$-pregnadiene-3,20-dione 11,17-diacetate The procedure of Example II(b), when carried out on the product of Example IV(b) gave 11β,17α-dihydroxy-21-methyl-$\Delta^{1,4}$-pregnadiene-3,20-dione 11,17-diacetate.

EXAMPLE V

17α-Hydroxy-21-methyl-$\Delta^{1,4}$-pregnadiene-3,20-dione 17-acetate

A solution of 17α-hydroxy-$\Delta^{1,4}$-pregnadiene-3,20-dione 17-acetate (1.0 g) in dry tetrahydrofuran (20 ml) was added to a stirred solution of lithium di-isopropylamide (2.5 mole equivalents) in tetrahydrofuran (20 ml) at 0° C. under nitrogen. The solution was allowed to come to room temperature over 30 minutes and then methyl iodide (10 ml) was added. After a further 30 minutes the reaction mixture was diluted with water, the product filtered, washed, dried, and purified on an alumina column to give 17α-hydroxy-21-methyl-$\Delta^{1,4}$-pregnadiene-3,20-dione 17-acetate. Treatment with Curvularia gave the corresponding 11β-hydroxy compound.

EXAMPLE VI

11β,17α-Dihydroxy-21-methyl-$\Delta^4$-pregnene-3,20-dione

A mixture of 10 ml methane sulphonic acid-chloride and 10 ml chloroform was added dropwise to a solution of 5 g 11β,17α,21-trihydroxy-21-methyl-$\Delta^4$-pregnene-3,20-dione in 75 ml pyridine, while stirring at a temperature of 0° C. After stirring for 3 hours at 0° C. the reaction mixture was poured into ice-water. After the addition of 140 ml 20% sulphuric acid and stirring, the mixture was extracted with chloroform. The extract was washed until neutral and then evaporated in vacuum till dryness.

The residue was dissolved in 300 ml acetic acid anhydride. 26 g Sodium iodide was added to the solution. The mixture was refluxed for 30 minutes, whereafter acetic acid anhydride was distilled off in vacuum and the residue was contacted with chloroform and water. The chloroform phase was washed with a solution of sodium sulphite, then washed with water, dried and evaporated to dryness. Crystallization of the residue from ethanol gave 2.4 g 11β,17α-dihydroxy-21-methyl-$\Delta^4$-pregnene-3,20-dione, m.p. 234°-237° C.

EXAMPLE VII

9α-Chloro-11β,17α-dihydroxy-21-methyl-$\Delta^{1,4}$-pregnadiene-3,20-dione 17-acetate 17α-Hydroxy-21-methyl-$\Delta^{1,4,9(11)}$-pregnatriene-3,20-dione 17-acetate (500 mg) were dissolved in 10% aqueous dioxan (20 ml) cooled to 10° C. and 72% perchloric acid (0.1 ml) was added followed by N-chlorosuccinimide (0.3 g) and the reaction mixture stirred overnight. The product was watered out, filtered, dried and recrystallised from methylene chloride to give 9α-chloro-11β,17α-dihydroxy-21-methyl-$\Delta^{1,4}$-pregnadiene-3,20-dione 17-acetate (350 mg).

EXAMPLE VIII

9α,11β-Dichloro-17α-hydroxy-21-methyl-$\Delta^{1,4}$-pregnadiene-3,20-dione 17-acetate 17α-Hydroxy-21-methyl-$\Delta^{1,4,9(11)}$-pregnatriene-3,20-dione 17-acetate (850 mg) was dissolved in a mixture of chloroform (45 ml) and pyridine (5 ml). Dry chlorine was passed into the solution for 45 seconds, and the reaction was then stirred for 30 minutes at room temperature. The excess chlorine was destroyed by addition of sodium sulphite solution, and the mixture was filtered to remove sulphur. The organic phase was washed successively with water, 2 N hydrochloric acid, water, saturated potassium bicarbonate solution and water to neutrality. The dried extracts was evaporated to dryness then the residue was purified on a silica column and crystallised from methanol to give 9α,11β-dichloro-17α-hydroxy-21-methyl-$\Delta^{1,4}$-pregnadiene-3,20-dione 17-acetate (500 mg).

EXAMPLE IX (a) Hydrocortisone 21-mesylate

A stirred suspension of hydrocortisone (250 g) in pyridine (1.25 l) at 5° C. was treated with methanesulphonyl chloride (125 ml) over 35 minutes so that the temperature remained between 5° and 10° C. By the end of the addition almost all the steroid was in solution. The mixture was stirred a further 20 minutes at 5°-8° C.

then the reaction was quenched by the addition of ice-cold water (5 l) with rapid stirring. The resulting solid was filtered off and washed with water and dried to give hydrocortisone 21-mesylate (279 g), m.p. 168°–172° C.

(b)

11β,17α-Dihydroxy-21-methyl-Δ⁴-pregnene-3,20-dione

To a stirred suspension of cuprous bromide (135.8 g) in ether (2.78 l) under nitrogen at −25° C. was added 1.3 N methyl lithium (1.456 l) in ether keeping the temperature between −10° and 0° C. The resulting solution of lithium dimethyl copper was cooled to −55° C. and treated slowly with a solution of hydrocortisone 21-mesylate (278 g) in dimethylformamide (6.95 l) keeping the temperature between −50° and −45° C. The slurry was warmed over 15 minutes to −10° C., stirred at −10° to 0° C. for 10 minutes, then slowly treated with a solution of ammonium chloride (834 g) in water (4.17 l) with the temperature kept below 0° C. Cooling was discontinued, and the mixture stirred for 15 minutes.

The aqueous layer was separated and extracted with methylene chloride (3×4.17 l). These extracts were added to the original ether layer and the combined organic extracts were washed with a solution of ammonium chloride (556 g) in water (2.78 l), then with water (2.78 l), dried, filtered and evaporated under reduced pressure to leave a concentrated solution of the product in dimethylformamide. Addition of water (5 l) gave 11β,17α-dihydroxy-21-methyl-Δ⁴-pregnene-3,20-dione (191 g) which was filtered off, washed with water and dried, m.p. 220°–248° C.

EXAMPLE X

11β,17α-Dihydroxy-21-methyl-Δ$^{1,4}$-pregnadiene-3,20-dione

The procedure of Example IX, when carried out on prednisolone gave 11β,17α-dihydroxy-21-methyl-Δ$^{1,4}$-pregnadiene-3,20-dione.

EXAMPLE XI (a)

11β,17α-Dihydroxy-21-methyl-Δ⁴-pregnene-3,20-dione 11-trifluoro-acetate

11β,17α-Dihydroxy-21-methyl-Δ⁴-pregnene-3,20-dione (140 g) was dissolved in dimethylformamide (1.4 l) at 35° C. and the stirred solution was cooled to −5° C. Trifluoroacetic anhydride (87.8 ml) was added dropwise over 35 minutes, keeping the temperature between −5° and 0° C. After a further 30 minutes at 0° C. the solution was poured into ice-cold water (7 l) and the resulting solid was filtered off, washed with water, and dried to give 11β,17α-dihydroxy-21-methyl-Δ⁴-pregnene-3,20-dione 11-trifluoroacetate (172.4 g), m.p. 171°–182° C.

(b)

11β,17α-Dihydroxy-21-methyl-Δ⁴-pregnene-3,20-dione 11-trifluoroacetate 17-n-butyrate 11β,17α-Dihydroxy-21-methyl-Δ⁴-pregnene-3,20-dione 11-trifluoroacetate (170 g) in pyridine (340 ml) was treated with n-butyric anhydride (680 ml), and 4-dimethylaminopyridine (8.5 g) and the stirred reaction mixture was immersed in a water bath at 50° C. for 21 hours. A further portion of 4-dimethylaminopyridine (8.5 g) was then added and the reaction continued as before. After a total of 44 hours the solution was cooled, poured into water (5.1 l) and the resulting mixture was stirred for 2 hours. Potassium carbonate (550 g) was added portionwise until effervescence ceased and the product was extracted into methylene chloride (1200 ml). The organic extracts were washed successively with 2 N hydrochloric acid (2×200 ml), water (200 ml), 5% sodium carbonate solution (200 ml) and water (2×200 ml), dried over sodium sulphate and evaporated to give 11β,17α-dihydroxy-21-methyl-Δ⁴-pregnene-3,20-dione 11-trifluoroacetate 17-n-butyrate (204.8 g).

(c)

11β,17α-Dihydroxy-21-methyl-Δ⁴-pregnene-3,20-dione 17-n-butyrate

11β,17α-Dihydroxy-21-methyl-Δ⁴-pregnene-3,20-dione 11-trifluoroacetate 17-n-butyrate (204.8 g) in methanol (1 l) was treated with potassium carbonate powder (100 g) and the resulting suspension was stirred at room temperature for 1 hour. Water (5 l) containing acetic acid (100 ml) was added and the mixture was stirred for 1 hour, then left overnight when the gummy product crystallised.

The solid was filtered off, washed with water, and dissolved in methylene chloride (1 l). This solution was dried over sodium sulphate, poured on to a column of alumina (500 g) (Grade H), which was eluted successively with methylene chloride (0.5 l) methylene chloride/ether 1:1 (1 l), and ether (1.5 l).

The combined eluates were evaporated to a solid (123.7 g) which was purified by chromatography on silica and recrystallised from acetone/ether to give 11β,17α-dihydroxy-21-methyl-Δ⁴-pregnene-3,20-dione 17-n-butyrate (76.3 g), m.p. 192°–196° C.

EXAMPLE XII

11β,17α-Dihydroxy-21-methyl-Δ⁴-pregnene-3,20-dione 17-acylates

The procedure of Example XI, when carried out on 11β,17α-dihydroxy-21-methyl-Δ⁴-pregnene-3,20-dione and using in step (b) acetic anhydride, propionic anhydride, valeric anhydride, phenylpropionic anhydride and pivalic anhydride, respectively, gave the 17-acetate, 17-propionate, 17-valerate, 17-phenylpropionate and 17-pivalate, respectively, of 11β,17α-dihydroxy-21-methyl-Δ⁴-pregnene-3,20-dione.

EXAMPLE XIII

11β,17α-Dihydroxy-21-methyl-Δ$^{1,4}$-pregnadiene-3,20-dione 17-acylates

The procedure of Example XI, when carried out on 11β,17α-dihydroxy-21-methyl-Δ$^{1,4}$-pregnadiene-3,20-dione and in the alternative using in step (b) acetic anhydride, propionic anhydride, valeric anhydride, phenylpropionic anhydride and pivalic anhydride, respectively, gave the 17-n-butyrate, 17-acetate, 17-propionate, 17-valerate, 17-phenylpropionate and 17-pivalate, respectively, of 11β,17α-dihydroxy-21-methyl-Δ$^{1,4}$-pregnadiene-3,20-dione.

EXAMPLE XIV

11β,17α-Dihydroxy-21-methyl-Δ⁴-pregnene-3,20-dione 11-trifluoroacetate 17-acylates 11β,17α-Dihydroxy-21-methyl-Δ⁴-pregnene-3,20-dione 11-trifluoroacetate (8 g), n-butyric anhydride (40 ml) and p-toluenesulphonic acid (0.8 g) were stirred together at room temperature for 4 hours. Water (400 ml) was added followed by an excess of potassium carbonate and the mixture was stirred for 1 hour. The product was extracted into methylene chloride (3×75 ml) and the combined extracts were washed with water until neutral, dried over magnesium sulphate, and evaporated to give 11β,17α-dihydroxy-21-methyl-Δ$^4$-pregnene-3,20-dione 11-trifluoroacetate 17-n-butyrate (10.7 g). Similarly were prepared the corresponding 17-acetate, 17-propionate, 17-valerate, 17-phenylpropionate and 17-pivalate.

EXAMPLE XV

11β,17α-Dihydroxy-21-methyl-Δ$^{1,4}$-pregnadiene-3,20-dione 11-trifluoroacetate 17-acylates 11β,17α-Dihydroxy-21-methyl-Δ$^{1,4}$-pregnadiene-3,20-dione 11-trifluoroacetate (7 g), n-butyric anhydride (35 ml) and p-toluenesulphonic acid (0.7 g) were stirred together at 40° C. for 16 hours. Water (300 ml) was added followed by an excess of potassium carbonate and the mixture was stirred for 1 hour. The product was extracted into methylene chloride (3×75 ml) and the combined extracts were washed with water until neutral, dried over magnesium sulphate, and evaporated under reduced pressure to give 11β,17α-dihydroxy-21-methyl-Δ$^{1,4}$-pregnadiene-3,20-dione 11-trifluoroacetate 17-n-butyrate as an oil (10.3 g).

Similarly were prepared the corresponding 17-acetate, 17-propionate, 17-valerate, 17-phenylpropionate, and 17-pivalate.

EXAMPLE XVI (a)

11β,17α-Dihydroxy-21-methyl-Δ$^4$-pregnene-3,20-dione 11-trichloroethoxyformate

11β,17α-Dihydroxy-21-methyl-Δ$^4$-pregnene-3,20-dione (4 g) in pyridine (60 ml) was treated at 15° C. with trichloroethyl chloroformate (6 ml) with cooling so that the temperature remained below 20° C. After 18 hours the reaction mixture was cooled in an ice-bath and ice-cold water (240 ml) added rapidly.

The mixture was extracted with ether (3×100 ml) and the combined extracts were washed successively with 2 N hydrochloric acid (2×150 ml), water (100 ml), 5% sodium carbonate solution (100 ml), and water (2×100 ml), dried over sodium sulphate and evaporated to give the crude product (10.0 g). Chromatography on silica gave pure 11β,17α-dihydroxy-21-methyl-Δ$^4$-pregnene-3,20-dione 11-trichloroethoxy formate.

(b)

11β,17α-Dihydroxy-21-methyl-Δ$^4$-pregnene-3,20-dione 11-trichloroethoxyformate 17-acylates 11β,17α-Dihydroxy-21-methyl-Δ$^4$-pregnene-3,20-dione 11-trichloroethoxyformate (8 g) in pyridine (20 ml) was treated with n-butyric anhydride (40 ml) and 4-dimethylaminopyridine (0.4 g) and the stirred reaction mixture was heated at 45° C. for 18 hours. A further portion of catalyst (0.4 g) was then added and the reaction mixture was heated for a further 24 hours. The cooled solution was added to water (300 ml), the mixture was stirred for 2 hours, and then made alkaline by the careful addition of potassium carbonate. The product was extracted into methylene chloride and the extracts were washed successively with 2 N hydrochloric acid (2×50 ml), water (50 ml), 5% sodium carbonate solution (50 ml) and water (2×50 ml), dried over sodium sulphate, and evaporated to give 11β,7α-dihydroxy-21-methyl-Δ$^4$-pregnene-3,20-dione 11-trichloroethoxyformate 17-n-butyrate.

Similarly were prepared the corresponding 17-acetate, 17-propionate, 17-valerate, 17-phenylpropionate, 17-pivalate.

(c)

11β,17α-Dihydroxy-21-methyl-Δ$^4$-pregnene-3,20-dione 17-acylates

11β,17α-Dihydroxy-21-methyl-Δ$^4$-pregnene-3,20-dione 11-trichloroethoxyformate 17-n-butyrate (3.5 g) in methanol (70 ml) was treated with zinc dust (3.5 g) and the stirred suspension was boiled for 2 hours. The zinc was removed by filtration through dicalite and the filtrate was evaporated to dryness. The resulting gum was dissolved in a hot solution of potassium carbonate (2 g) in methanol (140 ml), then the solution was cooled, and left 40 minutes at room temperature. Sufficient acetic acid to neutralise the base was then added, the solution was concentrated under vacuum and water (800 ml) was added to precipitate the product which was filtered off, washed with water and dried. Purification by chromatography on silica and recrystallisation from acetone/ether gave 11β,17α-dihydroxy-21-methyl-Δ$^4$-pregnene-3,20-dione 17-n-butyrate (0.71 g).

Similarly the corresponding 11-trichloroethoxyformate 17-acetate gave the 11β,17α-dihydroxy 17-acetate; the 11-trichloroethoxyformate 17-propionate gave the 11β,17α-dihydroxy 17-propionate; the 11-trichloroethoxyformate 17-valerate gave the 11β,17α-dihydroxy 17-valerate; the 11-trichloroethoxyformate 17-phenylpropionate gave the 11β,17α-dihydroxy 17-phenylpropionate; the 11-trichloroethoxyformate 17-pivalate gave the 11β,17α-dihydroxy 17-pivalate.

EXAMPLE XVII

11β,17α-Dihydroxy-21-methyl-Δ$^4$pregnene-3,20-dione 11-trichloroethoxyformate 17-acylates To a stirred solution of 11β,17α-dihydroxy-21-methyl-Δ$^4$-pregnene-3,20-dione 11-trichloroethoxyformate (2.96 g) in n-butyric anhydride (15 ml) was added p-toluenesulphonic acid (300 mg), and stirring was continued for 4 hours. The product was precipitated by addition to water (150 ml), pyridine (15 ml) was added, the mixture was stirred for 1 hour, then extracted with methylene chloride (4×50 ml). The combined extracts were washed with 2 N hydrochloric acid (100 ml), water (50 ml), 5% sodium carbonate solution (3×100 ml), and water (2×50 ml), dried over sodium sulphate, and evaporated to give 11β,17α-dihydroxy-21-methyl-Δ$^4$-pregnene-3,20-dione 11-trichloroethoxyformate 17-n-butyrate (3.5 g).

Similarly were prepared the corresponding 17-acetate, 17-propionate, 17-valerate, 17-phenylpropionate and 17-pivalate.

EXAMPLE XVIII

11β,17α-Dihydroxy-21-methyl-Δ$^{1,4}$-pregnadiene-3,20-dione 11-trichloroethoxyformate 17-acylates The procedure of Example XVII, when carried out on 11β,17α-dihydroxy-21-methyl-Δ$^{1,4}$-pregnadiene-3,20-dione 11-trichloroethoxyformate, gave the corresponding 17-n-butyrate, 17-acetate, 17-propionate, 17-valerate, 17-phenylpropionate and 17-pivalate, respectively.

EXAMPLE XIX

11β,17α-Dihydroxy-21-methyl-Δ$^{1,4}$-pregnadiene-3,20-dione 17-acylates

11β,17α-Dihydroxy-21-methyl-Δ$^{1,4}$-pregnadiene-3,20-dione 11-trifluoroacetate 17-pivalate (10 g) in methanol (250 ml) was treated with sodium formate (70 g) and water (5 ml) and the stirred mixture was heated under reflux for 6 hours. Water (1.5 l) was added, and the precipitated product was extracted into ethyl acetate. The combined organic extract was washed with water, dried over magnesium sulphate and evaporated to dryness. Chromatography on silica and crystallisation from acetone/ether gave 11β,17α-dihydroxy-21-methyl-Δ$^{1,4}$-pregnadiene-3,20-dione 17-pivalate (2.64 g), m.p. 240°–248° C.

Similarly the corresponding 11-trifluoroacetate 17-acetate gave the 11β,17α-dihydroxy 17-acetate; the 11-trifluoroacetate 17-propionate gave the 11β,17α-dihydroxy 17-propionate; the 11-trifluoroacetate 17-n-butyrate gave the 11β,17α-dihydroxy 17-n-butyrate; the 11-trifluoroacetate 17-valerate gave the 11β,17α-dihydroxy 17-valerate; the 11-trifluoroacetate 17-phenylpropionate gave the 11β,17α-dihydroxy 17-phenylpropionate.

EXAMPLE XX

11β,17α-Dihydroxy-21-methyl-Δ$^4$-pregnene-3,20-dione 17-acylates

11β,17α-Dihydroxy-21-methyl-Δ$^{1,4}$-pregnadiene-3,20-dione 17-n-butyrate (1.9 g) in ethanol (190 ml) and benzene (190 ml) was treated with tris(triphenylphosphine)rhodium (1) chloride (0.95 g) under nitrogen. A hydrogen atmosphere was introduced into the flask and the solution was stirred for 24 hours at room temperature. A further portion of catalyst (0.95 g) was added and stirring was continued under hydrogen for a further 24 hours. The solvent was then evaporated to dryness under reduced pressure and the residue was dissolved in methylene chloride. This solution was run through a short silica column, the product was eluted with methylene chloride and the eluate was evaporated to dryness. Chromatography and crystallisation from acetone/ether gave 11β,17α-dihydroxy-21-methyl-Δ$^4$-pregnene-3,20-dione 17-n-butyrate (0.7 g).

Similarly the Δ$^{1,4}$-pregnadiene 17-acetate gave the Δ$^4$-pregnene 17-acetate; the Δ$^{1,4}$-pregnadiene 17-propionate gave the Δ$^4$-pregnene 17-propionate; the Δ$^{1,4}$-pregnadiene 17-valerate gave the Δ$^4$-pregnene 17-valerate; the Δ$^{1,4}$-pregnadiene 17-pivalerate gave the Δ$^4$-pregnene 17-pivalate; the Δ$^{1,4}$-pregnadiene 17-phenylpropionate gave the Δ$^4$-pregnene 17-phenylpropionate.

EXAMPLE XXI (a)

11β,17α-Dihydroxy-21-ethyl-Δ$^{1,4}$-pregnadiene-3,20-dione

To a stirred suspension of powdered cuprous iodide (1.3 g) in ether (20 ml), under nitrogen and at −30° C., was added slowly 1.25 N ethyl lithium in ether (10.9 ml), the reaction temperature being maintained at −30° to −25° C.

The mixture was stirred at −30° C. for 5 minutes, then cooled to −55° C. and treated over 10 minutes with a solution of prednisolone 21-mesylate (2 g) in dimethyl formamide (50 ml), the temperature of the mixture being kept at −50° to −45° C. The mixture was allowed to warm to −10° C., stirred for 10 minutes at −10° to 0° C., then treated slowly with a solution of ammonium chloride (6 g) in water (30 ml), the temperature being kept at −10° to 0° C.

Cooling was discontinued and the mixture was stirred for 1 hour, then the aqueous layer was separated and extracted with methylene chloride (3×20 ml). These extracts were combined with the original organic layer, and the combined organic solution was washed with ammonium chloride solution (20 ml), filtered, washed with sodium sulphite solution (20 ml), then with water (20 ml), dried over sodium sulphate, and evaporated under reduced pressure to give a solid (1.63 g).

Chromatography on silica and crystallisation from methylene chloride-methanol/ethyl acetate gave 11β,17α-dihydroxy-21-ethyl-Δ$^{1,4}$-pregnadiene-3,20-dione m.p. 245°–262° C.

(b)

11β,11α-Dihydroxy-21-ethyl-Δ$^{1,4}$-pregnadiene-3,20-dione 17-acrylates

According to the procedure of Example XI the following 17-acylates were prepared: 17-propionate, 17-n-butyrate, 17-valerate and 17-pivalate.

EXAMPLE XXII

11β,17α-Dihydroxy-21-ethyl-Δ$^4$-pregnene-3,20-dione 17-acylates

The procedure of Example XXI, when carried out on hydrocortisone 21-mesylate gave 11β,17α-dihydroxy-21-ethyl-Δ$^4$-pregnene-3,20-dione 17-propionate, 17-n-butyrate, 17-valerate and 17-pivalate respectively.

EXAMPLE XXIII

17α-Hydroxy-21-methyl-Δ$^{1,4}$-pregnadiene-3,11,20-trione 17-acylates

To a stirred suspension of cuprous bromide (0.99 g) in ether (20 ml), under nitrogen and at −25° C., was added slowly 1.7 N methyl lithium in ether (8.1 ml), the reaction temperature being kept between −10° C. and 0° C.

The resulting solution of lithium dimethyl copper was cooled to −55° C. and treated over 8 minutes with a solution of prednisone 21-mesylate (2.0 g) in dimethyl formamide (50 ml), the temperature of the mixture being maintained at −50° C. to −45° C.

The resulting slurry was allowed to warm over 10 minutes to −10° C., stirred at −10° C. to 0° C. for 10 minutes, then treated slowly with a solution of ammonium chloride (6 g) in water (30 ml), the temperature being kept at −10° C. to 0° C. Cooling was discontinued, and the mixture was stirred for 1 hour.

The aqueous layer was separated and extracted with methylene chloride (3×20 ml). The extracts were added to the original organic layer, and the combined organic solution was washed with ammonium chloride solution (20 ml), then with water (2×20 ml), dried over sodium sulphate, and evaporated under reduced pressure to a solid (1.54 g). Chromatography on silica and crystallisation from acetone-ether gave 17α-hydroxy-21-methyl-Δ$^{1,4}$-pregnadiene-3,11,20-trione, m.p. 212°–220° C., which was then converted into 17-acylates thereof according to the procedure described in Example XVI (b).

EXAMPLE XXIV

17α-Hydroxy-21-methyl-Δ⁴-pregnene-3,11,20-trione 17-acylates

The procedure of Example XXIII, when carried out on cortisone 21-mesylate gave 17α-hydroxy-21-methyl-Δ⁴-pregnene-3,11,20-trione 17-acylates.

EXAMPLE XXV

9α-Fluoro-11β,17α-dihydroxy-21-methyl-Δ¹,⁴-pregnadiene-3,20-dione 17-n-butyrate

To a stirred suspension of cuprous bromide (0.91 g) in ether (20 ml), under nitrogen and at −25° C., was added slowly 0.83 N methyl lithium in ether (15.4 ml), the reaction temperature being maintained at −10° C. to 0° C.

The resulting solution of lithium dimethyl copper was cooled to −55° C. and treated over 10 minutes with a solution of 9α-fluoro-11β,17α,21-trihydroxy-Δ¹,⁴-pregnadiene-3,20-dione 21-mesylate (2.0 g) in dimethyl formamide (50 ml), keeping the temperature of the mixture at −50° C. to −45° C. The resulting slurry was allowed to warm over 10 minutes to −10° C., stirred at −10° C. to 0° C. for 10 minutes, then treated slowly with a solution of ammonium chloride (6 g) in water (30 ml), the temperature being maintained between −10° C. and 0° C. Cooling was discontinued, and the mixture was stirred for 15 minutes. The aqueous layer was separated and extracted with methylene chloride (3×20 ml). The extracts were added to the original organic layer, and the combined organic solution was washed with ammonium chloride solution (20 ml), then with water (2×20 ml), dried over sodium sulphate and evaporated under reduced pressure to give a gummy solid (1.31 g).

Crystallisation from methylene chloride/methanol gave 9α-fluoro-11β,17α-dihydroxy-21-methyl-Δ¹,⁴-pregnadiene-3,20-dione, which was then converted into its 17-n-butyrate (cf. Example XI).

EXAMPLE XXVI

9α-fluoro-11β,17α-dihydroxy-21-methyl-Δ⁴-pregnene-3,20-dione 17-pivalate

In a similar way as described in Example XXV 9α-fluoro-11β,17α,21-trihydroxy-Δ⁴-pregnene-3,20-dione 21-mesylate was converted into 9α-fluoro-11β,17α-dihydroxy-21-methyl-Δ⁴-pregnene-3,20-dione 17-pivalate.

EXAMPLE XXVII

9α-Fluoro-17α-hydroxy-21-methyl-Δ¹,⁴-pregnadiene-3,11,20-trione 17-valerate

To a stirred suspension of cuprous bromide (2.76 g) in ether (60 ml), under nitrogen and at −25° C., was added slowly 1.7 N methyl lithium in ether (22.6 ml), the reaction temperature being kept between −10° C. and 0° C. The resulting solution of lithium dimethyl copper was cooled to −55° C. and treated over 7 minutes with a solution of 9α-fluoro-17α,21-dihydroxy-Δ¹,⁴-pregnadiene-3,11,20-trione 21-mesylate (6.0 g) in dimethyl formamide (210 ml), the temperature of the mixture being maintained at −50° C. to −45° C.

The resulting slurry was warmed over 5 minutes to −10° C., stirred at −10° C. to 0° C. for 10 minutes, then treated slowly with a solution of ammonium chloride (18 g) in water (90 ml), the temperature being kept at −10° C. to 0° C. Cooling was discontinued, and the mixture was stirred for 15 minutes.

The aqueous layer was separated and extracted with methylene chloride (3×100 ml). The extracts were added to the original organic layer and the combined organic solution was washed with a solution of ammonium chloride (40 g) in water (200 ml), then with water (100 ml), filtered, and evaporated under reduced pressure to give a solution of the product in dimethylformamide (50 ml).

The solution was poured into stirred water (250 ml), and the resulting solid was filtered, washed with water, and dried (4.68 g).

Chromatography on silica and crystallisation from acetone-ether gave 9α-fluoro-21-methyl-17α-hydroxy-Δ¹,⁴-pregnadiene-3,11,20-trione, which was converted into its 17-valerate (cf. Example XI).

EXAMPLE XXVIII

9α-Fluoro-17α-hydroxy-21-methyl-Δ⁴-pregnene-3,11,20-trione 17-propionate

In a similar way as described in Example XXVII 9α-fluoro-17α,21-dihydroxy-Δ⁴-prepnene-3,11,20-trione 21-mesylate was converted into 9α-fluoro-17α-hydroxy-21-methyl-66⁴-pregnene-3,11,20-trione 17-propionate.

EXAMPLE XXIX

11β,17α-Dihydroxy-21-methyl-Δ¹,⁴-pregnadiene-3,20-dione 17-acylates

The procedure of Example XVI, when carried out on 11β,17α-dihydroxy-21-methyl-Δ¹,⁴-pregnadiene-3,20-dione, gave the corresponding 17-n-butyrate, 17-acetate, 17-propionate, 17-valerate, 17-phenylpropionate and 17-pivalate, respectively.

We claim:

1. A novel 21-alkylated steroid of the formula:

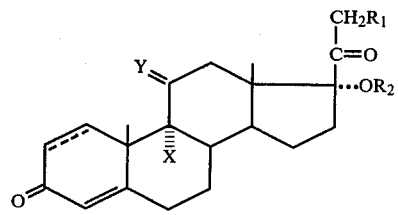

wherein $R_1$=alkyl (1-4 C); $R_2$=carboxyacyl (1-18 C); X=H, F or Cl; Y=O, H(OH), H(lower acyloxy), H(F) or H(Cl) with proviso that Y is not H(F) when X is F; and the dotted line indicates the optional presence of a double bond.

2. The compound of claim 1, wherein $R_1$ is methyl.

3. The compound of claim 1, wherein $R_1$ is methyl and $R_2$ is carboxyacyl (1-10 C).

4. The compound of claim 1, wherein $R_1$ is methyl, $R_2$ is carboxyacyl (1-10 C) and X is H.

5. The compound of claim 1, wherein $R_1$ is methyl, $R_2$ is carboxyacyl (1-10 C), X is H and Y is H(βOH).

6. The compound of claim 5, wherein $R_5$ is a member selected from the group consisting of propionyl, butyryl, pentanoyl and pivaloyl.

7. A pharmaceutical composition comprising an anti-inflammatory effective amount of a compound of claim 1 and a pharmaceutically effective carrier therefor.

8. A pharmaceutical composition comprising an anti-inflammatory effect amount of a compound of claim 5 or 6 and a pharmaceutically effective carrier therefor.

9. A process for preparing a 21-alkylated steroid as claimed in claim 1 of the formula

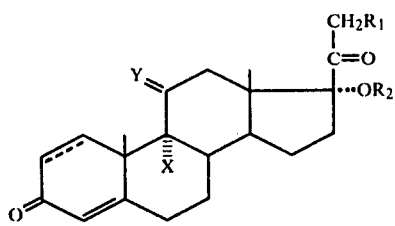

wherein $R_1$ is $C_1$–$C_4$ alkyl; $R_2$=carboxyacyl of 1 to 18 carbon atoms; X is H, F or Cl; Y is O, H(OH), H (lower acyloxy), H(F) or H(Cl) with the proviso that Y is not H(F) when X is F; and the dotted line indicates the optional presence of a double bond; which comprises (1) reacting a compound of the formula

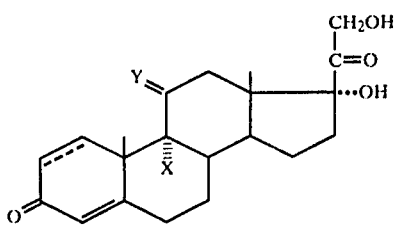

wherein X and Y are as defined above with an aryl or alkyl sulphonic acid halide at a temperature in the range of between 0° and 20° C. in the presence of a base to obtain the corresponding 21-sulphonate;

(2) reacting said 21-sulphonate with lithium-dialkyl copper in an inert solvent at a temperature in the range of between −75° C. and 0° C. to obtain the corresponding 21-alkyl-17α-hydroxy compound;

(3) acylating the 17α-hydroxy group while temporarily protecting any hydroxy group in position 11; and (4) introducing other substitutents required in the final product and not yet present by the following steps:
  (a) reacting with a suitable quinone derivative or a suitable dehydrogenating micro-organism for the introduction of the $\Delta^1$-double bond;
  (b) acylation of a hydroxy group in position 11;
  (c) oxidation of a hydroxy group in position 11, or
  (d) hydroxlysis of an acyloxy group in position 11.

* * * * *